United States Patent [19]

Mayn

[11] Patent Number: 5,476,491
[45] Date of Patent: Dec. 19, 1995

[54] THERAPEUTIC COLD PAD FOR USE IN OPERATION OF KEYBOARD

[75] Inventor: Alice M. Mayn, Foster City, Calif.

[73] Assignee: Contour Pak, Inc., San Mateo, Calif.

[21] Appl. No.: 323,130

[22] Filed: Oct. 12, 1994

[51] Int. Cl.⁶ ........................................ A61F 7/00
[52] U.S. Cl. ........................................ 607/111; 248/118
[58] Field of Search ................ 607/96, 108–112, 607/114; 248/118, 118.1, 118.3, 118.5, 205.2, 918

[56] References Cited

U.S. PATENT DOCUMENTS

| | | | |
|---|---|---|---|
| 1,460,915 | 7/1923 | Luton | 607/111 X |
| 4,492,221 | 1/1985 | Kerley | 607/111 X |
| 4,621,781 | 11/1986 | Springer | 248/118 |
| 5,150,707 | 9/1992 | Anderson | 607/114 |
| 5,193,771 | 3/1993 | Hassel et al. | 248/118 |

*Primary Examiner*—Angela D. Sykes
*Attorney, Agent, or Firm*—Beaton & Folsom

[57] ABSTRACT

A cold pad for use with a tool such as office equipment including computer controls like a keyboard or mouse. The cold pad has a thickness which is used to elevate the user's wrists from a work surface to lessen the onset of work-related disorders such as carpaltunnel syndrome. At the same time, the pad contains a gelatinous substance which absorbs heat and reduce pain and inflammation caused by existing injuries, and which forms a deformable cushion upon which the user's wrists can rest.

6 Claims, 1 Drawing Sheet

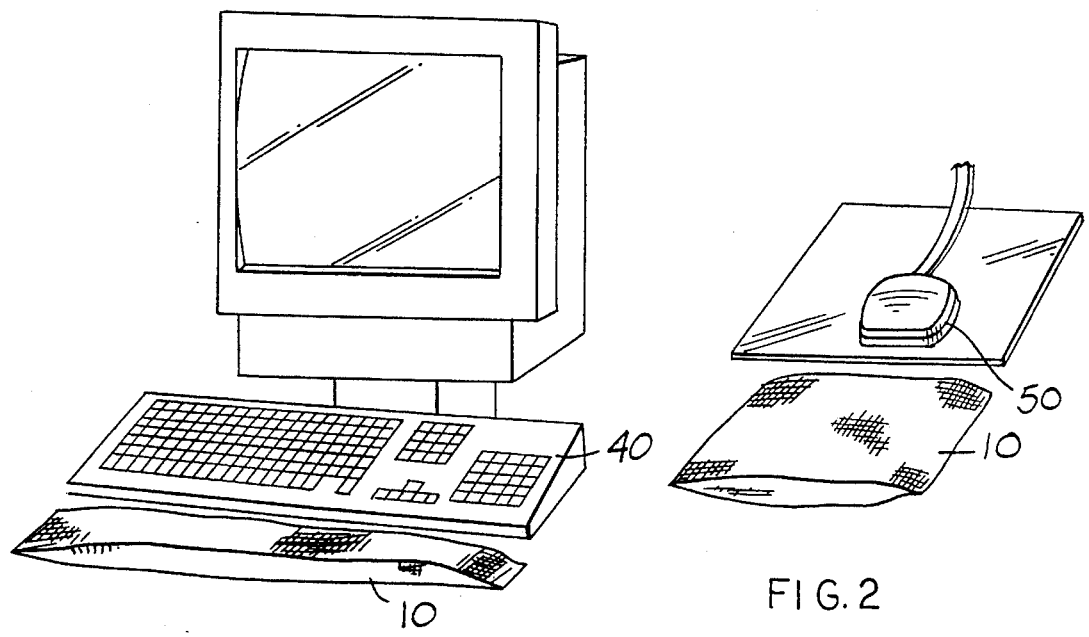
FIG. 1
FIG. 2
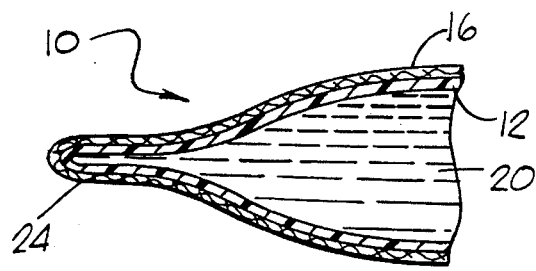
FIG. 3
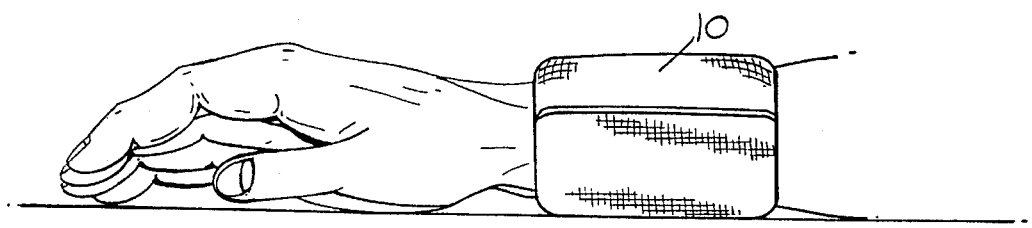
FIG. 4
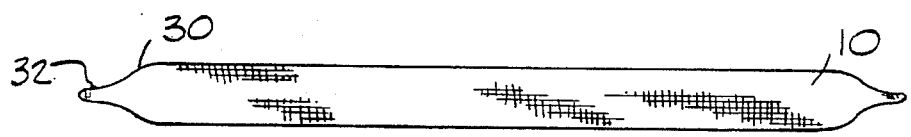
FIG. 5

THERAPEUTIC COLD PAD FOR USE IN OPERATION OF KEYBOARD

FIELD OF THE INVENTION

The present invention relates to the field of therapeutic devices and methods to prevent and relieve tissue trauma and stress resulting from occupations requiring repetitive hand and wrist motion such as the operation of word processing and other computer controls like keyboards and mouses. In particular, the present device and method includes a flexible pad filled with a gel which may be cooled upon which a user can rest his or her wrist so that the users hand and fingers extend outwardly from the pad to operate the computer controls.

BACKGROUND OF THE INVENTION

Cold packs have been used widely in the medical field for the therapeutic treatment of swelling and inflammation, and for the reduction of pain resulting from traumatic injuries or surgery. Cooling the traumatized area reduces the sensitivities of the nerve endings and also lessens swelling caused by cellular fluid expulsion. Cooling also constricts capillary vessels to reduce internal bleeding. Cold packs are particularly useful for causing this cooling because they can be applied locally without significant effect on the rest of the body, and they are also relatively convenient and inexpensive.

Most developments in the field of cold packs have related to means for attaching the cold pack to the body or the shape of the cold pack itself. Patents directed toward means for attaching the cold pack to the body include U.S. Pat. No. 4,347,848 by Hubbard, which is a generally rectangular envelope having an open end and a pair of tie strings on each end which can be tied to one another or to a part of the body. The overall configuration of the rectangular envelope and the attaching tie strings lends itself to attachment to a limb of the body, but not to attachment to other portions of the body. Similarly, U.S. Pat. No. 4,585,003 by Meistrell is an elongated element with extended legs which wrap around on itself and adhere with velcro brand hook and loop fasteners or other adhesive means. U.S. Pat. No. 4,517,972 by Finch carries the velcro idea further; velcro brand hook and loop fasteners, magnetic means or other adhesive means are adhered to the body and they, in turn, releasably attach to the cold pack. U.S. Pat. No. 4,645,498 by Kosak includes rectangular panels seated around the periphery to form an envelope with velcro brand hook and loop fasteners or other attachment means that allow the envelope to wrap around the limb and seal on itself.

Patents directed toward the shape of the cold pack, as distinguished from the means for attaching the cold pack to the body, include U.S. Pat. No. 4,240,436 by Singleton, which relates to a specially contoured cold pack for application to the perineal region. U.S. Pat. No. 3,491,761 by Baker relates to a specially designed harness for application of ice to the head region. U.S. Pat. No. 3,871,381 by Roslonski relates to an inflatable compress which is designed to assume the shape of the body portion to which it is attached, and the claims of that patent mention that the compress may be a wrap-around bandage, an inflatable sleeve, an inflatable mitten or inflatable foot boot.

Many of the traumatic injuries to which cold packs are applied are in the limbs of the patient. Therefore, many of the advances in cold packs have been directed towards mechanisms for attaching the cold pack to a limb. Such cold packs typically include an elongated void, such as a rectangular envelope, with strings, velcro or other attachment means located on each hand. In that way, the cold pack wraps around the limb and attaches to itself. Very little of the prior art is related to cold packs used on portions of the body other than limbs, and very little of the prior art is related to cold packs designed to engage a portion of the body with a surface apart from the body.

The widespread use of computer-based word processing machines in recent years has resulted in a dramatic increase in certain kinds of chronic hand and wrist injuries, which are generally grouped under the heading "carpaltunnel syndrome". Such injuries are characterized by long term, chronic pain, and degradation of joints and connective tissue in the hand, wrist and fingers, resulting from repetitive stress and motion over an extended period of time. It has been found that the symptomatic inflammation and pain of carpaltunnel syndrome can be relieved by the application of a cold pack. A drawback to palliative therapy employing cold packs is that the cold packs render useless the patient's hands during the specific time of the therapy, since one cannot easily use one's hands when the hands are bound up with ice or other low temperature material in a pack. Thus, it is difficult to apply the cold pack for extended periods, as may be required for any appreciable effect.

It has also been determined that the pain and inflammation of carpaltunnel syndrome may be alleviated, and the syndrome may be partially or wholly prevented altogether, by modifying the relative positions of the computer control (i.e., the keyboard or mouse) in relation to the user's hand and wrist. Specifically, it has been found that it may be helpful to elevate the user's hand or wrist so that the user's fingers descend onto the controls, thereby reducing the amount of bending of the wrists that would otherwise be required for the user to place her hand over the controls while resting the wrist on the work surface. Also, it is believed that resting the wrist on a hard surface causes compression of tissue which is injurious. Both these concerns can be addressed by placement of a soft or deformable pad a half inch to one inch thick under the user's wrist.

Accordingly, a device and method for using the same would be desirable which combines the advantages of a cold pack in treating the symptoms and effects of carpaltunnel syndrome-type conditions with the therapeutic advantages of an elevating pad placed under the patient's wrist. Preferably, such a device and method would also alleviate tissue compression on the underside of the patient's wrists caused by resting the wrists on typical hard work surfaces, such as desks and typing tables. It would also be desirable if such a device were easily reconfigured, for example to wrap around a patient's wrist if that were the desired treatment method.

SUMMARY OF THE INVENTION

The present invention is a cold pad having an elongated body with a width and a thickness, for placement in front of a computer keyboard so that the longitudinal axis is parallel to the long dimension of the keyboard. The pad is filled with a gel which has a high heat capacity so that the pad can be refrigerated to a low temperature and maintained at the low temperature for an extended period thereafter. The gel has a high viscosity to allow the pad to deform somewhat upon the application of pressure. The pad is roughly one half inch to one inch thick, to provide suitable elevation of the user's wrists in front of the keyboard.

In another embodiment of the invention, the pad is not elongated, but instead is approximately square or round for use with a computer mouse. In that embodiment, the pad is also approximately one half inch to one inch thick. In both embodiments, the pad preferably includes at a minimum an inner sealing layer to contain the gel and an outer soft fabric layer. Although not necessary, there also may be an intermediate layer between the inner layer and outer layer having high moisture absorbing properties to act as a wick to draw perspiration away from the user's skin.

Both embodiments of the invention elevate the user's wrists to provide a more comfortable and less stressful angle between the wrist and the computer controls such as the keyboard or mouse. At the same time, the low temperature characteristic of the pad helps reduce inflammation and pain in the user's wrist. The conforming shape of the pad produced by the viscous gel lessens tissue compression in the user's wrists to reduce trauma and increase comfort, even if the pad is used in an uncooled state.

BRIEF DESCRIPTION OF THE DRAWINGS

FIG. 1 shows a cold pad in accordance with an embodiment of the present invention, shown in combination with a keyboard.

FIG. 2 shows another embodiment of a cold pad in accordance with the present invention, shown in combination with a computer mouse.

FIG. 3 shows a partial cross-sectional view of the invention.

FIG. 4 shows another application of the embodiment of FIG. 1.

FIG. 5 shows a side view of the invention.

DETAILED DESCRIPTION OF THE INVENTION

A partial cross-sectional view of the cold pad ten of the present invention is shown in FIG. 3. The cold pad 10 preferably has two plys. An inner most ply is a polyurathane sheet 12 about two to six millimeters thick to contain the gel 20 described below. Of course, this innermost ply may be made of materials other than polyethylene; any suitable moisture proof material having sufficient tensile and shear strength is acceptable, as would be apparent to persons skilled in the art.

An exterior layer 16 surrounds the entire cold pad 10 outside of the intermediate layer 14, and is the portion of the cold pad 10 that contacts the user's skin. This exterior layer 16 should be soft and comfortable against the skin, should be relatively non-thermally insulated, and, preferably, should be of a material that can be used in an adhesive application. For example, a velcro brand hook and loop fastener as described below, requires that the exterior layer 16 be a velcro brand hook and loop fastener adhesive material. It has been found that a relatively thin polyester flannel is suitable for this purpose. Of course, the exterior layer may be dyed in any color desired for medical, aesthetic or recognition purposes.

The two layers are sealed at the edge 24. The two layers 12 are preferably sealed by ultrasonic welding or heat welding, an adhesive or other suitable means depending upon the type of material chosen for that layer. The gel 20 is a viscous gelatinous material that can be cooled to a very low temperature in an ordinary freezer or the like, and which requires a high amount of heat to elevate its temperature. It is also preferable that the gelatinous material be viscous, so that it forms a deformable cushion when contained within the cold pad 10.

As shown in FIG. 5, one end 30 of the elongated cold pad 10 may have adhesive element attached to it such as the velcro brand hook and loop fastener element 32 shown in that figure. Such an attachment allows the elongated cold pad 10 to be wrapped around the user's wrist. As shown in FIG. 4 the cold pad 10 is wrapped around the limb in a doughnut shape, and retained thereon by attaching the velcro brand hook and loop fastener 32 to the outer layer 16 surface of the opposite end of the cold pad 10. In this way, the user has the advantages of elevating the wrist off the work surface by the thickness of the pad, with the added advantage that the cold pad extends completely around the user's wrist to relieve inflammation and swelling throughout.

The velcro brand hook and loop fastener may be sewn or otherwise attended to one end of the cold pad and releasably adhered to the opposite and in the normal velcro manner or may be a separate element which is releasably adhered to each end in the normal velcro manner. The cold pad 10 is in a more conventional mode in FIG. 1, which shows the cold pad 10 in combination with a computer keyboard 40. In this combination, the cold pad 10 elevates the user's wrist from the work surface by the thickness of the pad (approximately one half inch to one inch). The user therefore can adopt a more comfortable and less injurious angle in operating the keyboard 40. At the same time, the heat absorbing properties of the cold pad 10 cool the bottom of the user's wrists to alleviate pain and inflammation caused by existing carpal-tunnel syndrome-type injuries.

An alternative embodiment of the cold pad 10 is shown in FIG. 2, which shows the cold pad 10 in combination with a computer mouse 50. Again, the user's wrist is elevated from the work surface by the thickness of the pad (again, one half inch to one inch). At the same time, the user's wrists bottom is cooled by the heat absorbing properties of the cold pad 10.

What is claimed is:

1. A system for preventing and alleviating repetitive work injuries, comprising: a keyboard having a front edge; and an elongated cold pad with a longitudinal axis, the cold pad being positioned adjacent said keyboard front edge and having a thickness whereby a user's wrist is elevated from a work surface by said thickness, and the cold pad containing a gelatinous material which can be cooled to absorb heat from the user's wrist.

2. The system of claim 1, wherein the cold pad has at least one end with a fastener to attach to an opposite end so that the cold pad can be wrapped around a user's wrist and fastened on itself while the user operates the keyboard.

3. The system of claim 2 wherein the fastener is releasably attachable to both the one end and the opposite end.

4. A method for treating or preventing repetitive work injuries caused by operation of a computer keyboard by a user, comprising: cooling an elongated cold pad filled with a gelatinous material; placing said cold pad adjacent the keyboard; and operating the keyboard with the user's wrist resting on the cold pad so that the cold pad simultaneously cushions, elevates and cools the user's wrist.

5. The method of claim 4, further comprising wrapping the elongated cold pad around the user's wrist and attaching it to itself, so that the cold pad simultaneously elevates and cushions the user's wrist and cools completely around the user's wrist.

6. A method for treating or preventing repetitive work injuries caused by operation of a tool, comprising and cooling a cold pad filled with gelatinous material; placing said cold pad adjacent the tool; and operating the tool with the user's wrist resting on the cold pad so that the cold pad simultaneously cushions, elevates and cools the patient's wrist.

* * * * *